(12) United States Patent
Ibrahim et al.

(10) Patent No.: US 10,424,474 B2
(45) Date of Patent: *Sep. 24, 2019

(54) METHOD AND DEVICE FOR ION MOBILITY SEPARATION

(71) Applicant: Battelle Memorial Institute, Richland, WA (US)

(72) Inventors: Yehia M. Ibrahim, Richland, WA (US); Sandilya V. B. Garimella, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/759,194

(22) PCT Filed: May 2, 2016

(86) PCT No.: PCT/US2016/030455
§ 371 (c)(1),
(2) Date: Mar. 9, 2018

(87) PCT Pub. No.: WO2017/044159
PCT Pub. Date: Mar. 16, 2017

(65) Prior Publication Data
US 2018/0254178 A1 Sep. 6, 2018

Related U.S. Application Data

(63) Continuation of application No. 14/851,935, filed on Sep. 11, 2015, now Pat. No. 9,704,701.

(51) Int. Cl.
*H01J 49/26* (2006.01)
*H01J 49/02* (2006.01)
(Continued)

(52) U.S. Cl.
CPC ............ *H01J 49/26* (2013.01); *G01N 27/622* (2013.01); *H01J 49/0013* (2013.01); *H01J 49/022* (2013.01); *H01J 49/40* (2013.01)

(58) Field of Classification Search
CPC ...... H01J 49/26; H01J 49/0013; H01J 49/022; H01J 49/40; G01N 27/622
(Continued)

(56) References Cited

U.S. PATENT DOCUMENTS 4,777,363 A 10/1988 Eiceman et al.
5,206,506 A 4/1993 Kirchner
(Continued)

FOREIGN PATENT DOCUMENTS

AU 2014251354 B2 11/2017
AU 2016320584 A1 4/2018
(Continued)

OTHER PUBLICATIONS

English translation of the first Chinese office action from corresponding Chinese patent application No. 201480032436.7, dated Oct. 14, 2016, 5 pages.
(Continued)

*Primary Examiner* — Nicole M Ippolito
(74) *Attorney, Agent, or Firm* — Klarquist Sparkman, LLP (57) ABSTRACT

Methods and devices for ion separations or manipulations in gas phase are disclosed. The device includes a non-planar surface having a first, second and third region. An inner arrays of electrodes is positioned on the first region. A first set of electrodes of the inner array of electrodes is configured to receive RF voltages and generate a first potential upon the receipt of the RF voltage. A first and second outer arrays of electrodes are coupled to the second and third region, respectively. The first and second outer arrays are configured
(Continued)

to receive a first DC voltage and generate a second potential upon the receipt of the first DC voltages. The first and second generated potential manipulate movement of ions.

16 Claims, 10 Drawing Sheets

(51) Int. Cl.
    *H01J 49/00*     (2006.01)
    *H01J 49/40*     (2006.01)
    *G01N 27/62*     (2006.01)

(58) Field of Classification Search
    USPC .................................. 250/281, 282, 283, 290
    See application file for complete search history.

(56) References Cited

U.S. PATENT DOCUMENTS

| | | | |
|---|---|---|---|
| 5,572,035 | A | 11/1996 | Franzen |
| 5,834,771 | A | 11/1998 | Yoon et al. |
| 6,107,628 | A | 8/2000 | Smith et al. |
| 6,417,511 | B1 | 7/2002 | Russ, IV |
| 6,891,157 | B2 | 5/2005 | Bateman et al. |
| 6,960,760 | B2 | 11/2005 | Bateman et al. |
| 7,095,013 | B2 | 8/2006 | Bateman et al. |
| 7,151,255 | B2 | 12/2006 | Weiss et al. |
| 7,157,698 | B2 | 1/2007 | Makarov et al. |
| 7,180,078 | B2 | 2/2007 | Pau et al. |
| 7,365,317 | B2 | 4/2008 | Whitehouse et al. |
| 7,391,021 | B2 | 6/2008 | Stoermer et al. |
| 7,405,401 | B2 | 7/2008 | Hoyes |
| 7,548,818 | B2 | 6/2009 | Kieser |
| 7,786,435 | B2 | 8/2010 | Whitehouse et al. |
| 7,838,826 | B1 | 11/2010 | Park |
| 7,872,228 | B1 | 1/2011 | Kim et al. |
| 7,888,635 | B2 | 2/2011 | Belov et al. |
| 7,928,375 | B1 | 4/2011 | Mangan et al. |
| 8,003,934 | B2 | 8/2011 | Hieke |
| 8,049,169 | B2 | 11/2011 | Satake et al. |
| 8,222,597 | B2 | 7/2012 | Kim et al. |
| 8,319,180 | B2 | 11/2012 | Nikolaev et al. |
| 8,373,120 | B2 | 2/2013 | Verentchikov |
| 8,389,933 | B2 | 3/2013 | Hoyes |
| 8,410,429 | B2 | 4/2013 | Franzen et al. |
| 8,581,181 | B2 | 11/2013 | Giles |
| 8,809,769 | B2 | 8/2014 | Park |
| 8,835,839 | B1 * | 9/2014 | Anderson ............... H01J 49/06 250/290 |
| 8,901,490 | B1 | 12/2014 | Chen et al. |
| 8,907,273 | B1 | 12/2014 | Chen et al. |
| 8,969,800 | B1 | 3/2015 | Tolmachev et al. |
| 9,704,701 | B2 * | 7/2017 | Ibrahim ................... H01J 49/26 |
| 9,812,311 | B2 | 11/2017 | Anderson et al. |
| 9,966,244 | B2 | 5/2018 | Anderson et al. |
| 2001/0035498 | A1 | 11/2001 | Li |
| 2003/0132379 | A1 | 7/2003 | Li |
| 2004/0026611 | A1 | 2/2004 | Bateman et al. |
| 2004/0089803 | A1 | 5/2004 | Foley |
| 2004/0222369 | A1 | 11/2004 | Makarov et al. |
| 2005/0040327 | A1 | 2/2005 | Lee et al. |
| 2005/0109930 | A1 | 5/2005 | Hill, Jr. et al. |
| 2007/0138384 | A1 | 6/2007 | Keiser |
| 2008/0073515 | A1 | 3/2008 | Schoen |
| 2009/0173880 | A1 | 7/2009 | Bateman et al. |
| 2009/0206250 | A1 | 8/2009 | Wollnik |
| 2011/0049357 | A1 | 3/2011 | Giles |
| 2011/0192969 | A1 | 8/2011 | Verentchikov |
| 2014/0061457 | A1 | 3/2014 | Berdnikov et al. |
| 2014/0124663 | A1 | 5/2014 | Green et al. |
| 2014/0145076 | A1 | 5/2014 | Park |
| 2014/0299766 | A1 | 10/2014 | Anderson et al. |
| 2015/0028200 | A1 | 1/2015 | Green et al. |
| 2015/0364309 | A1 | 12/2015 | Welkie |
| 2016/0027604 | A1 | 1/2016 | Cho et al. |
| 2016/0049287 | A1 | 2/2016 | Ding et al. |
| 2016/0071715 | A1 | 3/2016 | Anderson et al. |
| 2017/0076931 | A1 | 3/2017 | Ibrahim et al. |
| 2017/0125229 | A1 | 5/2017 | Giles et al. |
| 2018/0061621 | A1 | 3/2018 | Anderson et al. |

FOREIGN PATENT DOCUMENTS

| | | |
|---|---|---|
| AU | 2016335524 A9 | 5/2018 |
| CA | 2908936 | 10/2014 |
| CA | 2997910 | 3/2017 |
| CA | 3000341 | 4/2017 |
| CN | 1361922 | 7/2002 |
| CN | 101126738 | 2/2008 |
| CN | 102163531 | 8/2011 |
| CN | 102945786 | 2/2013 |
| CN | 201680069722.X | 8/2016 |
| CN | 105264637 B | 9/2017 |
| CN | 107507751 A | 12/2017 |
| CN | 108352288 A | 7/2018 |
| DE | 112013004733 | 6/2015 |
| EP | 1566828 | 8/2005 |
| EP | 1825495 | 8/2007 |
| EP | 2065917 | 6/2009 |
| EP | 2913839 | 9/2015 |
| EP | 2984675 A1 | 2/2016 |
| EP | 3347913 A1 | 7/2018 |
| EP | 3359960 A1 | 8/2018 |
| GB | 2440970 | 2/2008 |
| GB | 2506362 | 4/2014 |
| JP | 2002-015699 | 1/2002 |
| JP | 2009532822 | 9/2009 |
| JP | 2009535759 | 10/2009 |
| JP | 2009537070 | 10/2009 |
| JP | 2011529623 | 12/2011 |
| JP | 2012503286 | 2/2012 |
| JP | 2016514896 A | 5/2016 |
| JP | 2018-518405 | 8/2016 |
| JP | 2018528427 A | 9/2018 |
| SG | 11201801852Q | 5/2016 |
| SG | 11201802494Q | 8/2016 |
| SG | 11201508277X | 2/2018 |
| WO | WO 2006/064274 | 6/2006 |
| WO | WO 2007/133469 | 11/2007 |
| WO | WO 2010/014077 | 2/2010 |
| WO | WO 2010/032015 | 3/2010 |
| WO | WO 2011/089419 | 7/2011 |
| WO | WO 2012/116765 | 9/2012 |
| WO | WO 2013/018529 | 2/2013 |
| WO | WO 2014/048837 | 4/2014 |
| WO | WO 2014/168660 | 10/2014 |
| WO | WO 2015/056872 | 4/2015 |
| WO | WO 2015/097462 | 7/2015 |
| WO | WO 2016/069104 | 5/2016 |
| WO | WO 2017/044159 | 3/2017 |
| WO | WO 2017/062102 | 4/2017 |

OTHER PUBLICATIONS

English translation of the search report from corresponding Chinese patent application No. 201480032436.7, dated Sep. 29, 2016, 2 pages.

European Search Report for European Patent Application No. 14782685.3, dated Oct. 25, 2016.

Examination Report No. 1 for related Australian Application No. 2016320584, dated Jun. 27, 2018, 3 pages.

First Office Action for related Canadian Application No. 2,997,910, dated May 4, 2018, 4 pages.

Hamid, et al., "Characterization of Travelling Wave Ion Mobility Separations in Structures for Lossless Ion Manipulations," Analytical Chemistry, 87(22):11301-11308 (Nov. 2015).

International Search Report and Written Opinion for PCT/US2016/047070 (dated Nov. 7, 2016).

International Search Report and Written Opinion for related International Application No. PCT/US2014/011291, dated Jun. 6, 2014, 2 pages.

(56) References Cited

OTHER PUBLICATIONS

Search Report from corresponding Singapore patent application No. 11201508277X, dated Mar. 6, 2016, 7 pages.
Tolmachev, et al., "Characterization of Ion Dynamics in Structures for Lossless Ion Manipulations," Analytical Chemistry, 86(18):9162-9168 (Sep. 2014).
International Search Report and Written Opinion issued in related International Application No. PCT/US2016/030455, dated Jul. 25, 2016, 19pp.
First Office Action for related Japanese Application No. 2018-513012, dated Aug. 2, 2018, 2 pages; with English translation, 2 pages.
First Office Action for related Chinese Application No. 201680065673.2, dated Sep. 30, 2018, 6 pages.
Chen, et al., "Mobility-Selected Ion Trapping and Enrichment Using Structures for Lossless Ion Manipulations", Analytical Chemistry, Jan. 2016, 88, pp. 1728-1733.
Deng et al., "Serpentine Ultralong Path with Extended Routing (SUPER) High Resolution Traveling Wave Ion Mobility-MS using Structures for Lossles Ion Manipulations", Analytical Chemistry, Mar. 2017, 89, pp. 4628-4634.
Examination Report No. 2 for related Australian Application No. 2016320584, dated Sep. 3, 2018, 2 pages.
Examination Report No. 1 for related Australian Application No. 2016335524, dated May 15, 2018, 4 pages.
First Office Action for related Canadian Application No. 3,000,341, dated Jul. 30, 2018, 5 pages.
First Office Action for Chinese Application No. 201680065673.2, dated Sep. 30, 2018, 6 pages (English translation not yet available).
International Search Report and Written Opinion for related International Application No. PCT/US2018/041607, dated Sep. 20, 2018, 18 pp.
Webb et al., "Mobility-Resolved Ion Selection in Uniform Drift Field Ion Mobility Spectrometry/Mass Spectrometry: Dynamic Switching in Structures for Lossless Ion Manipulations," Analytical Chemistry, Oct. 2014, 86, 9632-9637.
Wojcik et al., "Lipid and Glycolipid Isomer Analyses Using Ultra-High Resolution Ion Mobility Spectrometry Separations", International Jouranl of Molecular Sciences, Jan. 2017, 18, 12 pp.
Written Opinion from the Intellectual Property Office of Singapore for related Application No. 11201802494Q, dated Aug. 21, 2018, 8 pages.
Written Opinion from the Intellectual Property Office of Singapore for related Application No. 11201801852Q, dated Nov. 22, 2018, 26 pages.
International Search Report and Written Opinion for related International Application No. PCT/US2018/046752, dated Dec. 4, 2018, 12 pp.
English translation of the first Chinese office action from corresponding Chinese patent application No. 201710799275.X, dated Nov. 2, 2018, 12 pages.

\* cited by examiner

METHOD AND DEVICE FOR ION MOBILITY SEPARATION

STATEMENT REGARDING FEDERALLY SPONSORED RESEARCH OR DEVELOPMENT

This invention was made with Government support under Contract DE-AC0576RL01830 awarded by the U.S. Department of Energy. The Government has certain rights in the invention.

CROSS-REFERENCE TO RELATED APPLICATIONS

This application is a U.S. National Stage of International Application No. PCT/US2016/030455, filed May 2, 2016, which was published in English under PCT Article 21(3), which in turn claims priority to U.S. application Ser. No. 14/851,935, filed Sep. 11, 2015 now U.S. Pat. No. 9,704,701, titled "METHOD AND DEVICE FOR ION MOBILITY SEPARATIONS" hereby incorporated by reference in its entirety for all of its teachings.

TECHNICAL FIELD

This invention relates to ion mobility separations and other ion manipulations in the gas phase. More specifically, this invention relates to an ion mobility separation method and ion manipulations in a device having a single, non-planar surface containing electrodes.

BACKGROUND

The utility of mass spectrometry expands with the capability to conduct more complex ion manipulations. Current ion mobility technologies and ion manipulations rely on surrounding surfaces that serve to define the electric fields. However, these approaches can become ineffective when, for example, trying to miniaturize these devices for field deployment. In addition, it is extremely difficult to achieve high ion mobility spectrometry (IMS) resolution by extending the drift length traveled by ions in a reasonable and practical physical length. Hence, the utility of IMS is hindered by conventional ion optics designs.

What is needed is an ion mobility separation or manipulation device with an open structure, including an ion separation channel, and which also prevents ion losses.

SUMMARY

The present invention is directed to an ion mobility separation or manipulation device that includes a single surface. The single surface is non-planar or not flat. The device also includes arrays of electrodes coupled to the surface. The device further includes a combination of RF and DC voltages applied to arrays of electrodes to create confining and driving fields that move ions through the device. The surface can have, in one embodiment, arrays of electrodes on each side of the surface.

In one embodiment, one or more electrodes or others surfaces external to the device can help partially or fully define or affect the electric fields created by the electrodes on the surface. These external electrodes or surfaces, which have voltages applied to them, allow different or more complex fields to be established or created. This would allow, for example, one array of electrodes on the surface to be turned off while the other array is turned on. This can be useful for, among other things, peak compression or the bunching of ions. In one embodiment, the arrays of electrodes coupled to the surface extend above the surface, and may also vary in the distance above the surface. Further, the one or more arrays of electrodes coupled to the surface can be turned on or turned off by the external surfaces and/or electrodes.

The single, non-planar surface can be of many different shapes. The surface can have a curved, cylindrical, spiral, funnel, hemispherical, elliptical, or non-symmetrical shape.

In one embodiment, a transparent enclosure or cover is disposed on the device. A voltage can be applied to the cover to guard against interfering potential from, e.g., ground or nearby electronics. In one embodiment, the device is located in a partially or completely transparent enclosure or cover.

In one embodiment, the arrays of electrodes include one or more arrays of inner RF electrodes and a plurality of arrays of outer DC electrodes. The inner array of RF electrodes and the outer arrays of DC electrodes extend substantially along the length of the surface. In one embodiment, a first outer array of DC electrodes is positioned on one side of the inner array of RF electrodes, and a second outer array of DC electrodes is positioned on the other side of the inner array of electrodes.

In one embodiment, the DC voltages are applied to the first and second outer electrodes arrays, and the RF voltages are applied to the inner array of electrodes.

In one embodiment, the RF waveform on at least one inner electrode array is out of phase with RF waveform on a neighboring inner RF electrode array. The RF voltage applied to each inner RF electrode array may be phase shifted with its neighboring inner electrode array to form a pseudopotential. In one embodiment, the RF voltage applied to the inner electrode array is approximately 180 degrees out of phase with its neighboring inner electrode array to form the pseudopotential.

The device may further comprise one or more arrays of inner DC electrodes that extend substantially along the length of the surface, in either a linear or non-linear path. Each inner array of DC electrodes is positioned between an adjacent pair of the RF electrode arrays. A RF waveform on at least one inner array of RF electrodes is out of phase with RF waveform on a neighboring or adjacent inner array of RF electrodes.

In one embodiment, a first DC voltage applied to the outer array of DC electrodes is the same, and a second DC voltage applied to the inner array of DC electrodes is a DC gradient or different across the inner DC arrays.

In one embodiment, a first DC voltage applied to the outer array of DC electrodes is different across the outer array or is a DC gradient, and a second DC voltage applied to the inner array of DC electrodes is a DC gradient or different across the inner DC arrays.

The first DC voltage may have a higher or lower amplitude than the second DC field.

In one embodiment, the inner array of DC electrodes is misaligned or offset from the outer array of electrodes.

In one embodiment, a DC voltage is superimposed on at least one of the inner arrays of RF electrodes.

The device may be coupled to at least one of the following: a charge detector, ion image detector, an optical detector, and a mass spectrometer.

In one embodiment, the ions are introduced from outside the device at an angle to the device.

The ions may be formed inside or outside of the device using at least one of the following: photoionization, Corona discharge, laser ionization, electron impact, field ionization, chemical ionization, and electrospray.

The DC voltages may be static DC voltages or time-dependent DC potentials or waveforms.

In one embodiment, the surface is formed by curving a flexible printed circuit board material, three-dimensional printing, or other means to deposit conductive material on a non-conductive surface.

In another embodiment of the present invention, a method of moving and separating ions in gas phase is disclosed. The method includes coupling arrays of electrodes to a single, non-planar surface. The method also includes applying a combination of RF and DC voltages to the arrays of electrodes to create confining and driving fields that move ions through the single curved or non-planar surface.

In another embodiment of the present invention, an ion mobility separation device is disclosed. The device includes a single, non-planar surface. The device also includes arrays of electrodes which include one or more arrays of inner RF electrodes and a plurality of arrays of outer DC electrodes. The inner array of RF electrodes and the outer array of DC electrodes extend substantially along the length of the surface. A first and second outer array of DC electrodes is positioned on either side of the inner array of RF electrodes. The device further includes one or more arrays of inner DC electrodes that extend substantially along the length of the surface. Each inner array of DC electrodes is positioned between an adjacent pair of inner RF electrode arrays. A combination of RF and DC voltages are applied to the arrays of electrodes to create confining and driving fields that move ions through the device.

In one embodiment, a RF waveform on at least one inner array of RF electrodes is out of phase with RF waveform on a neighboring or adjacent inner array of RF electrodes.

A first DC voltage applied to the outer array of DC electrodes is the same or different, and a second DC voltage applied to the inner array of DC electrodes is a DC gradient or different across the inner DC arrays.

In another embodiment of the present invention, an ion mobility device is disclosed. The device includes a single, non-planar surface. The device also includes arrays of inner RF electrodes and a plurality of arrays of outer DC electrodes, coupled to the single surface, wherein the inner array of RF electrodes and the outer array of DC electrodes extend substantially along the length of the single surface. A first and second outer array of DC electrodes is positioned on either side of the inner array of RF electrodes. A combination of RF and DC voltages applied to the arrays of electrodes to create confining and driving fields that move ions through the device, and a DC field is superimposed on the inner arrays of RF electrodes to further confine and move the ions through the device.

In another embodiment, the device can include two or more non-planar surfaces with different orientations to each other that provide a "waterfall" effect of the ions moving through each surface.

DETAILED DESCRIPTION OF THE PREFERRED EMBODIMENTS

The following description includes the preferred best mode of embodiments of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Disclosed are methods and devices for ion mobility separations. The device has an open structure and may comprise a drift cell formed by a single surface that is not flat or planar. The single surface is thus open and may be curved or angled to form an ion separation channel and help prevent ion losses, which is in contrast to prior drift cells that have two planar surfaces of electrodes forming the channel.

The single, non-planar surface may be formed by curving a flexible printed circuit board material, by three-dimensional printing, or other means to deposit a conductive material on a non-conductive surface.

A combination of RF and DC fields are applied to arrays of electrodes coupled to the surface to create, along with the shape of the curved surface, confining and driving fields that move ions through the device. Lateral confinement is achievable by a combination of electric fields applied to outer electrodes as well as the curvature of the surface.

In one embodiment, two separate arrays of electrodes positioned closer to the middle of the device confine and drive ions throughout the device.

Ions can be driven through the device either by application of static DC field or time-dependent DC field.

The device allows for ion injection at an angle to the plane of ion motion and construction of, in one example, a helical shaped separation device.

The open, non-planar device, which can be curved, also allows for the following: ion introduction at any location in the device; ion current/mobility/mass measurements, as well as optical measurements, at any location in the device; and the non-planar cross section allows non-rectilinear ion path (e.g. helix) which is not possible with planar devices due to the two top and bottom boards.

The device can also include a cover positioned or disposed on the device. On this cover a voltage can be applied to guard against interfering voltage or potential from, e.g., ground or nearby electronics.

Two or more devices can be combined or coupled together, with one device above and offset from the other at an angle, to provide a "waterfall" effect of the ions traveling from one device to another.

FIGS. 1A-1D show different views of an ion mobility device 100 having a single curved or non-planar surface 105 containing arrays of outer DC electrodes 110 and inner DC electrodes 130. The device 100 also includes arrays of RF electrodes 120 and 125 of opposite phase, RF+ and RF−, on either side of the inner DC electrodes 130, in accordance with one embodiment of the present invention. The arrays are coupled to and extend substantially along the length of the surface 105.

In one embodiment, the DC voltage applied to the outer array DC electrodes 110 is the same. The DC voltages applied to the inner array DC electrodes 130 may be different or may be a DC gradient applied across the inner array 130. The DC voltages or fields may be static DC fields or time-dependent DC fields or waveforms.

As shown in FIG. 1, each inner array of DC electrodes 130 is positioned between an adjacent pair—e.g., adjacent RF arrays 120 and 125 or adjacent RF arrays 125 and 120—of the inner array of RF electrodes. Also, a RF waveform on at least one inner array of RF electrodes 120 and 125 is out of phase with a neighboring or adjacent array of RF electrodes 120 or 125. In one embodiment, an inner RF electrode array 120 or 125 is approximately 180 degrees out of phase or phase shifted with its neighboring inner electrode array 120 or 125 to form a pseudopotential.

The surface 105, which is either curved or non-planar, is a single surface. In one embodiment, the surface 105 is not flat and may be comprised of, but is not limited to, a flexible printed board material.

FIGS. 2A-2D show different views of an ion mobility device 200 having a single curved or non-planar surface 205 containing arrays of outer DC electrodes 210 and arrays of inner RF electrodes 220 and 230 with a superimposed DC field on the inner array of RF electrodes 220 and 230, in accordance with one embodiment of the present invention. The RF field on at least one inner electrode array 220 is out of phase with its neighboring inner electrode 230. For example, the RF waveform phase applied to electrode arrays 220 are positive (+), and the RF waveform phase applied to electrode arrays 230 are negative (−). DC gradient or different voltages are applied to the electrodes 210.

FIGS. 3A-3D show different views of an ion mobility device 300 having a single curved or non-planar surface 305 containing arrays of outer DC electrodes 310 and arrays of inner DC electrodes 330 with different DC fields or a DC gradient applied across the arrays of electrodes 310 and 330. The device 300 also includes arrays of RF electrodes 320 and 325 of opposite phase, RF+ or RF−, on either side of the inner DC electrodes 330, in accordance with one embodiment of the present invention. As such, each inner array of DC electrodes 330 is positioned between an adjacent pair of the inner array of RF electrodes 320 and 325.

The DC field applied to the outer array of DC electrodes 310 is different across the outer array 310 or is a DC gradient. The DC field applied to the inner array of DC electrodes 330 is a DC gradient or is different.

FIGS. 4A-4D show different views of an ion mobility device 400 device having a single curved or non-planar surface 405 containing arrays of inner DC electrodes 430 that are offset or misaligned from the arrays of outer DC electrodes 410. Arrays of RF electrodes 420 and 425 of opposite phase (+ or −) are on either side of the inner DC electrodes 430.

The DC field applied to the outer array of DC electrodes 410 and inner array of DC electrodes 430 is different across the outer and inner DC arrays 410 and 430. In one embodiment, a DC gradient is applied across the outer and inner DC arrays 410 and 430. Each inner array of DC electrodes 430 is positioned between an adjacent pair of the inner array of RF electrodes 420 and 425.

Figure 1A:
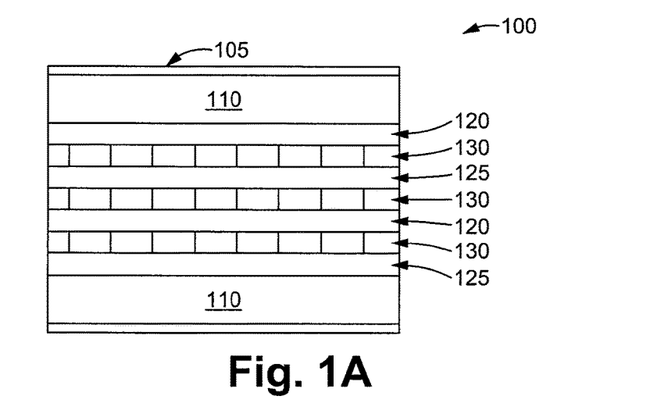
FIG. 1A is a top view schematic diagram of an ion mobility device having a single curved or non-planar surface containing arrays of outer and inner DC electrodes and arrays of RF electrodes of opposite phase on either side of the inner DC electrodes, in accordance with one embodiment of the present invention.
Figure 1B:
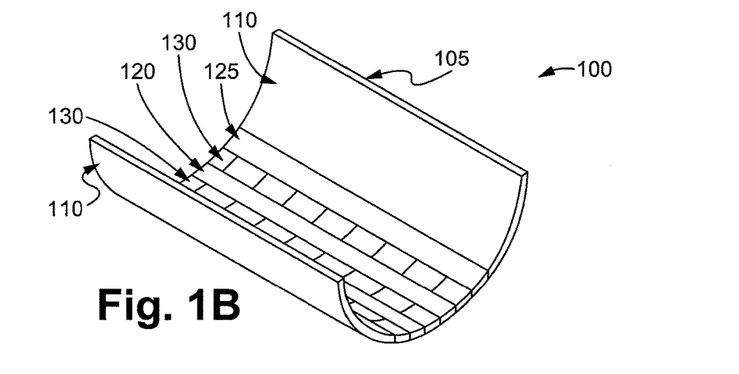
FIG. 1B is a perspective view schematic diagram of an ion mobility device having a single curved or non-planar surface containing arrays of outer and inner DC electrodes and arrays of RF electrodes of opposite phase on either side of the inner DC electrodes, in accordance with one embodiment of the present invention.
Figure 1C:
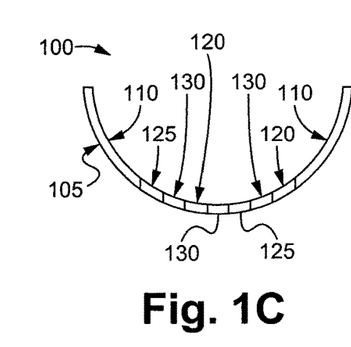
FIG. 1C is a front view schematic diagram of an ion mobility device having a single curved or non-planar surface containing arrays of outer and inner DC electrodes and arrays of RF electrodes of opposite phase on either side of the inner DC electrodes, in accordance with one embodiment of the present invention.
Figure 1D:
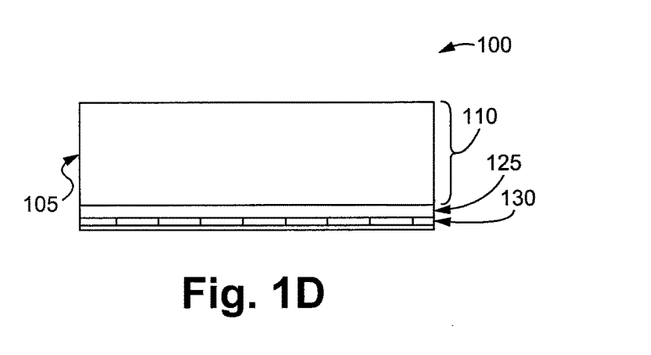
FIG. 1D is a side view schematic diagram of an ion mobility device having a single curved or non-planar surface containing arrays of outer and inner DC electrodes and arrays of RF electrodes of opposite phase on either side of the inner DC electrodes, in accordance with one embodiment of the present invention.
Figure 2A:
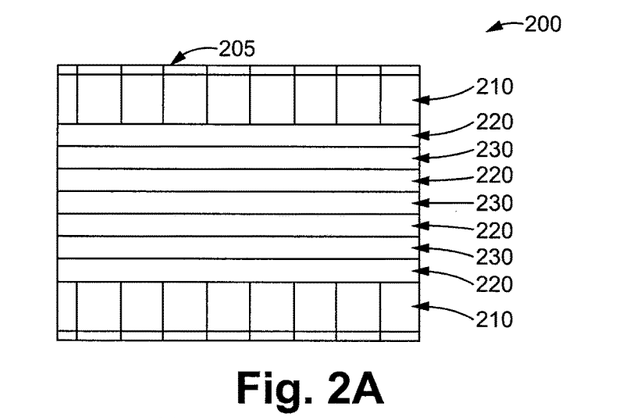
FIG. 2A is a top view schematic diagram of an ion mobility device having a single curved or non-planar surface containing arrays of outer DC electrodes and inner RF electrodes with a superimposed DC field on the inner array of RF electrodes, in accordance with one embodiment of the present invention.
Figure 2B:
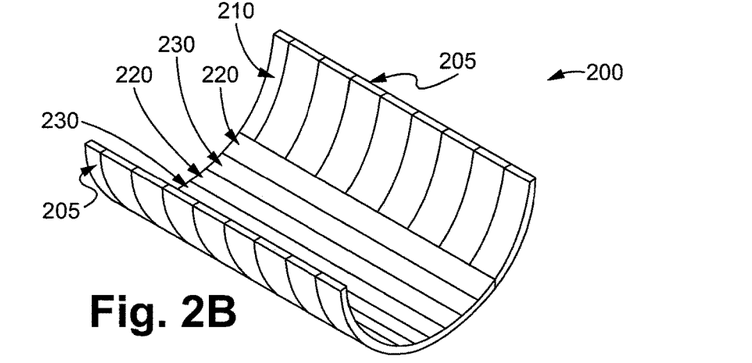
FIG. 2B is a perspective view schematic diagram of an ion mobility device having a single curved or non-planar surface containing arrays of outer DC electrodes and inner RF electrodes with a superimposed DC field on the inner array of RF electrodes, in accordance with one embodiment of the present invention.
Figure 2C:
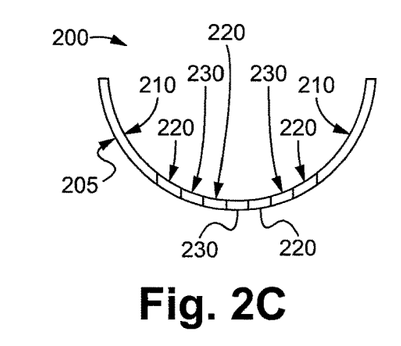
FIG. 2C is a front view schematic diagram of an ion mobility device having a single curved or non-planar surface containing arrays of outer DC electrodes and inner RF electrodes with a superimposed DC field on the inner array of RF electrodes, in accordance with one embodiment of the present invention.
Figure 2D:
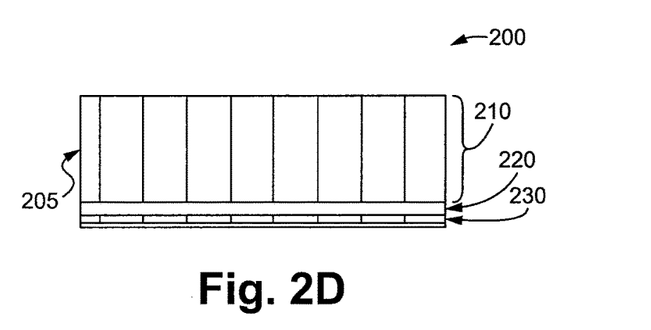
FIG. 2D is a side view schematic diagram of an ion mobility device having a single curved or non-planar surface containing arrays of outer DC electrodes and inner RF electrodes with a superimposed DC field on the inner array of RF electrodes, in accordance with one embodiment of the present invention.
Figure 3A:
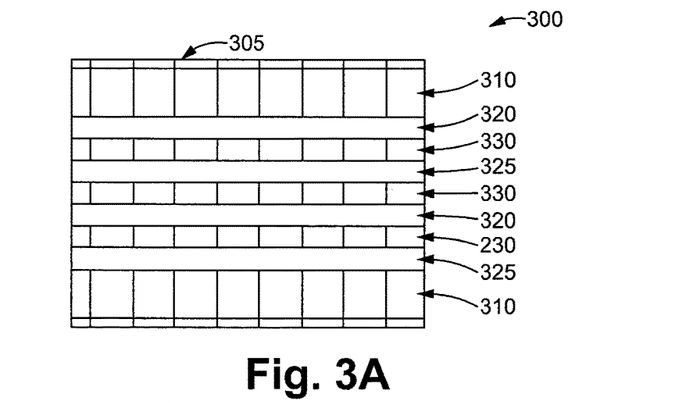
FIG. 3A is a top view schematic diagram of an ion mobility device having a single curved or non-planar surface containing arrays of outer and inner DC electrodes with different DC fields or a DC gradient applied across the electrodes and arrays of RF electrodes of opposite phase on either side of the inner DC electrodes, in accordance with one embodiment of the present invention.
Figure 3B:
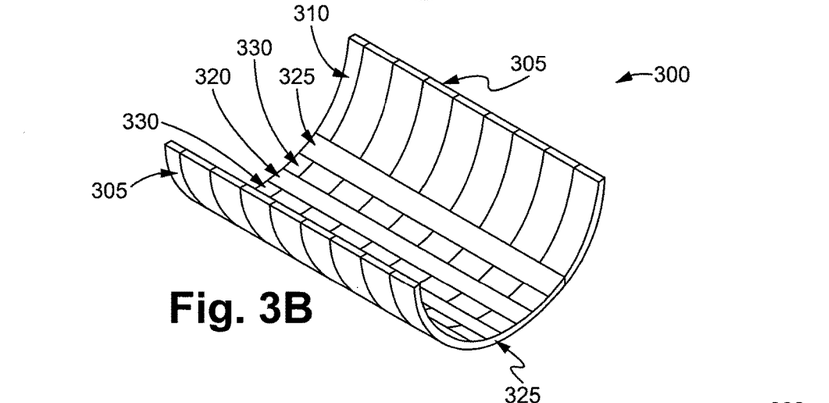
FIG. 3B is a perspective view schematic diagram of an ion mobility device having a single curved or non-planar surface containing arrays of outer and inner DC electrodes with different DC fields or a DC gradient applied across the electrodes and arrays of RF electrodes of opposite phase on either side of the inner DC electrodes, in accordance with one embodiment of the present invention.
Figure 3C:
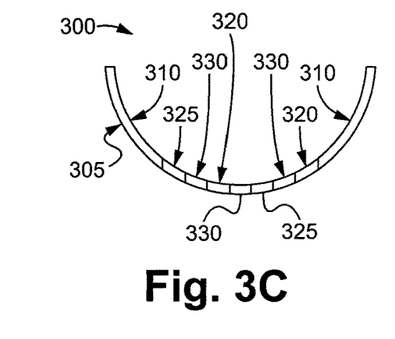
FIG. 3C is a front view schematic diagram of an ion mobility device having a single curved or non-planar surface containing arrays of outer and inner DC electrodes with different DC fields or a DC gradient applied across the electrodes and arrays of RF electrodes of opposite phase on either side of the inner DC electrodes, in accordance with one embodiment of the present invention.
Figure 3D:
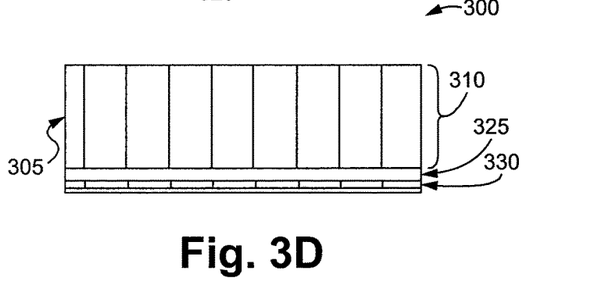
FIG. 3D is a side view schematic diagram of an ion mobility device having a single curved or non-planar surface containing arrays of outer and inner DC electrodes with different DC fields or a DC gradient applied across the electrodes and arrays of RF electrodes of opposite phase on either side of the inner DC electrodes, in accordance with one embodiment of the present invention.
Figure 4A:
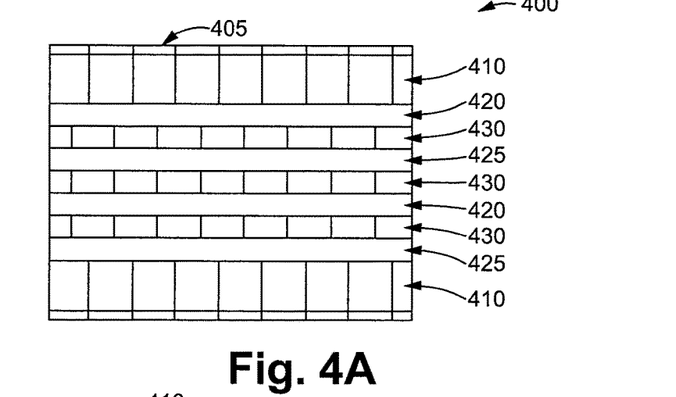
FIG. 4A is a top view schematic diagram of an ion mobility device having a single curved or non-planar surface containing arrays of misaligned or offset outer and inner DC electrodes with different DC fields or a DC gradient applied across the electrodes and arrays of RF electrodes of opposite phase on either side of the inner DC electrodes, in accordance with one embodiment of the present invention.
Figure 4B:
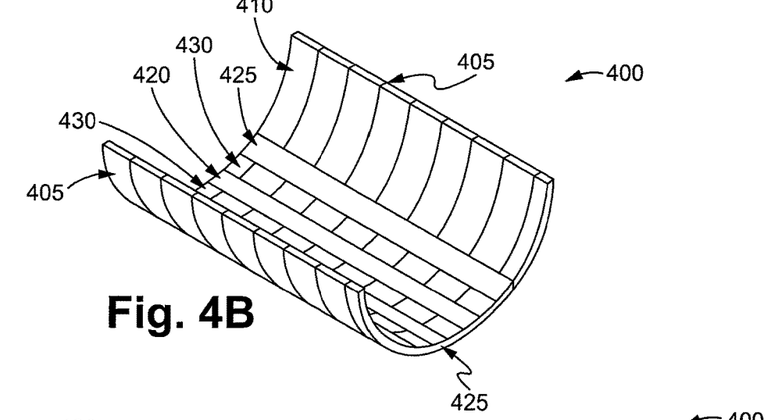
FIG. 4B is a perspective view schematic diagram of an ion mobility device having a single curved or non-planar surface containing arrays of misaligned or offset outer and inner DC electrodes with different DC fields or a DC gradient applied across the electrodes and arrays of RF electrodes of opposite phase on either side of the inner DC electrodes, in accordance with one embodiment of the present invention.
Figure 4C:
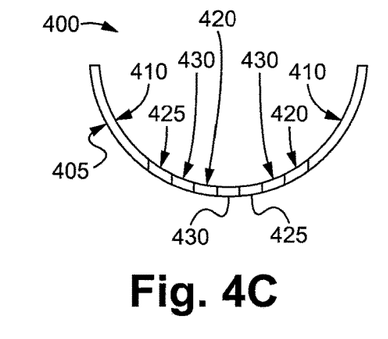
FIG. 4C is a front view schematic diagram of an ion mobility device having a single curved or non-planar surface containing arrays of misaligned or offset outer and inner DC electrodes with different DC fields or a DC gradient applied across the electrodes and arrays of RF electrodes of opposite phase on either side of the inner DC electrodes, in accordance with one embodiment of the present invention.
Figure 4D:
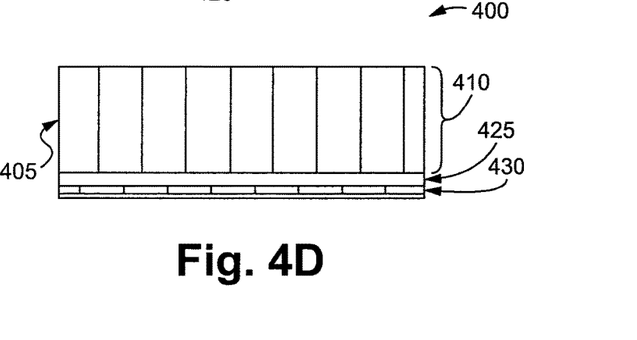
FIG. 4D is a side view schematic diagram of an ion mobility device having a single curved or non-planar surface containing arrays of misaligned or offset outer and inner DC electrodes with different DC fields or a DC gradient applied across the electrodes and arrays of RF electrodes of opposite phase on either side of the inner DC electrodes, in accordance with one embodiment of the present invention.
Figure 5:
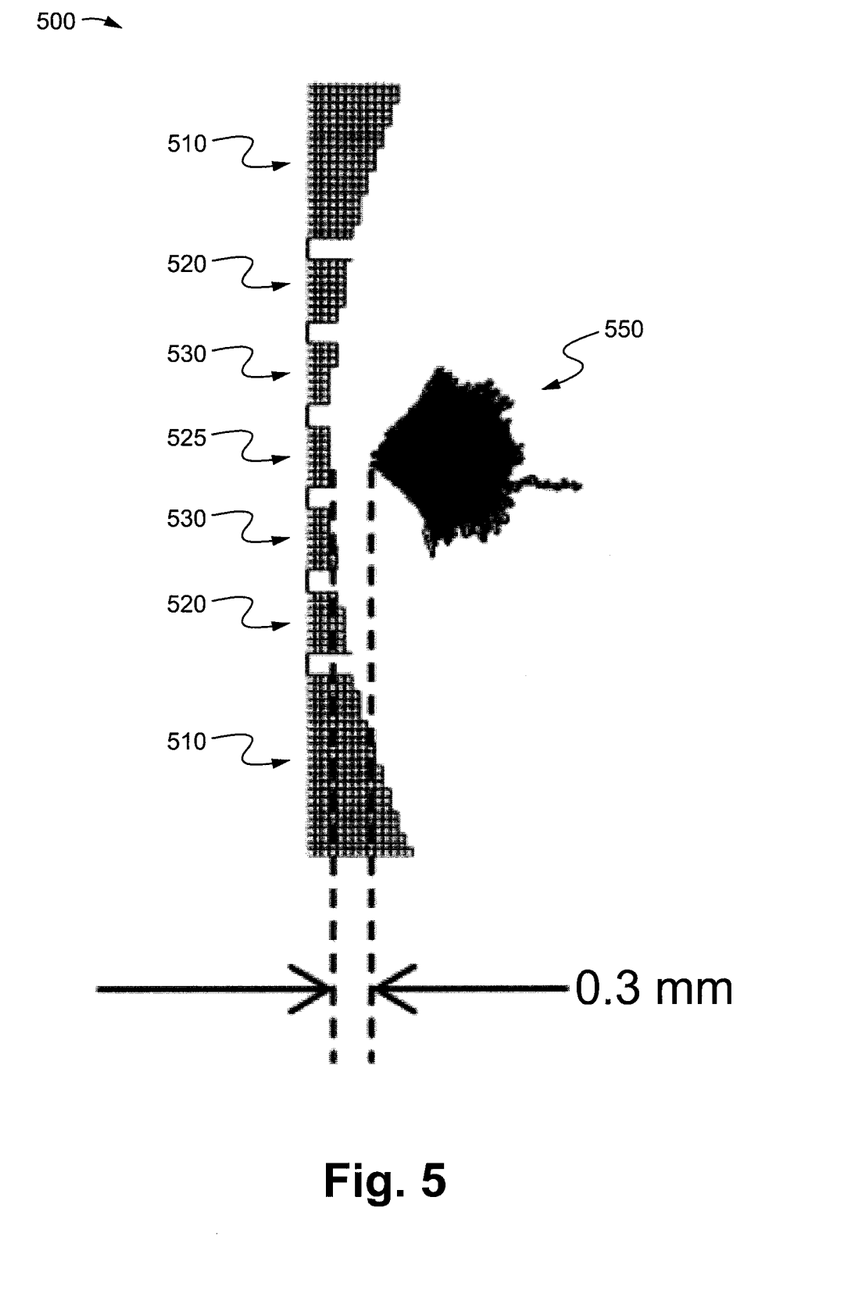
FIG. 5 shows a cross section of the ion mobility device of FIG. 1, with ions moving through the device at a distance from the surface, in accordance with one embodiment of the present invention.

FIG. 5 shows a cross section of the ion mobility device 500 of FIG. 1, with ions 550 moving through the device at a distance from the surface, in accordance with one embodiment of the present invention. The device 500 includes an outer array of DC electrodes 510, an inner array of RF electrodes 520 and 525, and an inner array of DC electrodes 530 positioned between array of RF electrodes 520 and 525 of opposite phase (+ or −).

In the example of FIG. 5, the ions are approximately 0.3 mm from the surface of the device 500. A combination of RF and DC fields applied to the arrays of electrodes 510, 520, 525, and 530, along with the shape of the curved surface, create confining and driving fields that move ions through the device 500. Lateral confinement is achievable by the curved nature of the surface and application of electric fields to the outer electrodes 510. The inner RF and DC electrode arrays 520, 525, and 530 confine and drive ions through the device. The ions can be driven either through a static DC field or a time-dependent DC waveform or field.

Figure 6:
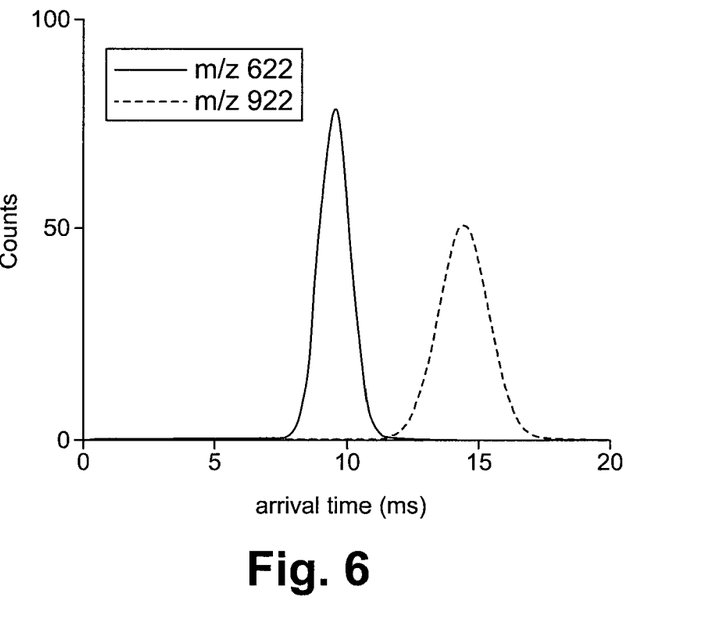
FIG. 6 is a plot of ion counts over arrival time using the embodiment of FIG. 1, showing separation of two ions with different mass-to-charge ratios according to their mobilities.

FIG. 6 is a plot of ion counts over arrival time using the embodiment of FIG. 1, showing the mobility separation of two ions with different mass-to-charge ratios—m/z 622 and m/z 922.

Figure 7A:
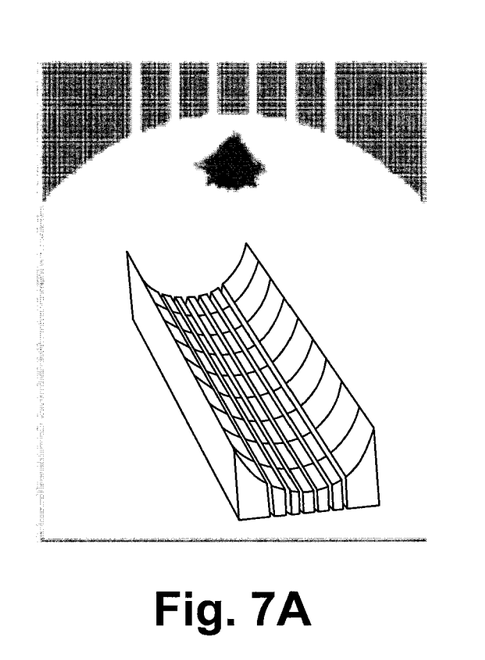
FIG. 7A is a three-dimensional schematic diagram of the device of FIG. 1, with ions moving through the device at a distance from the surface, in accordance with one embodiment of the present invention.

FIG. 7A is a three-dimensional schematic diagram of the device of FIG. 1, with ions moving through the device at a distance from the surface, in accordance with one embodiment of the present invention.

Figure 7B:
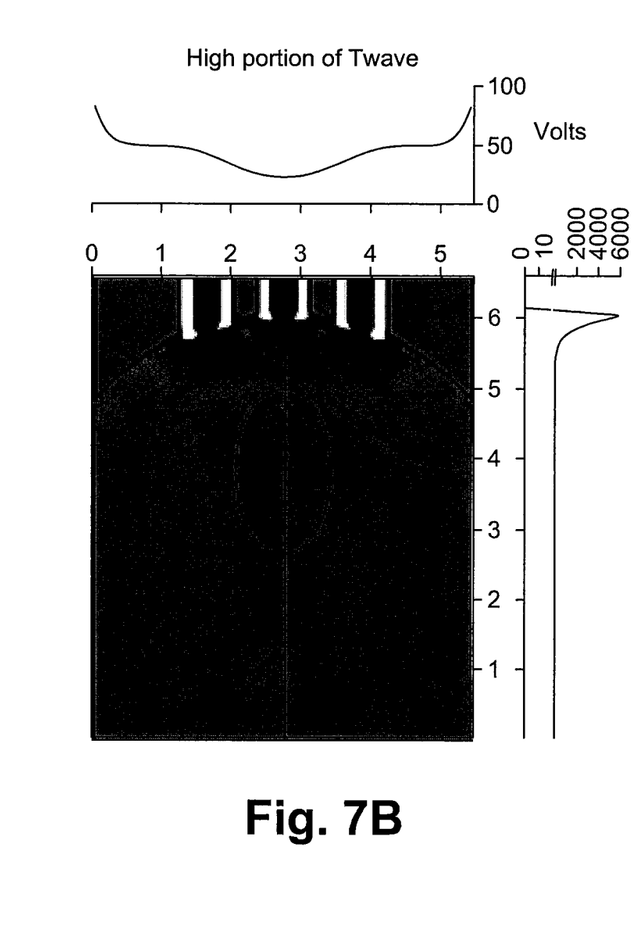
FIG. 7B is a plot showing ion confinement within the device of FIG. 7A at the high portion of a time-dependent electric field.

FIG. 7B is a plot showing ion confinement within the device of FIG. 7A at the high portion of a time-dependent electric field, a dynamic electric field.

Figure 7C:
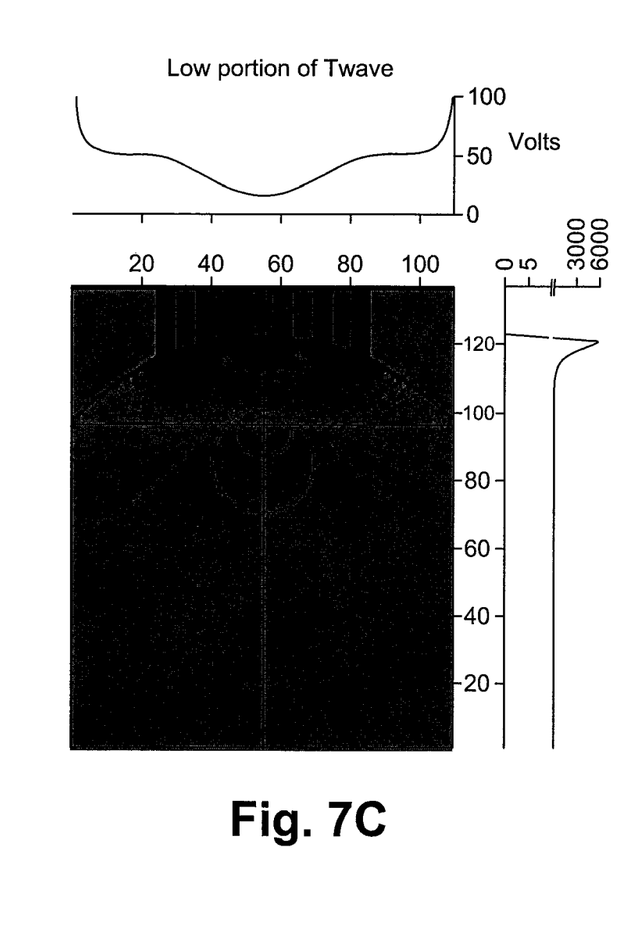
FIG. 7C is a plot showing ion confinement within the device of FIG. 7A at the low portion of a time-dependent electric field.

FIG. 7C is a plot showing ion confinement within the device of FIG. 7A at the low portion of a time-dependent electric field, a dynamic electric field.

Figure 8:
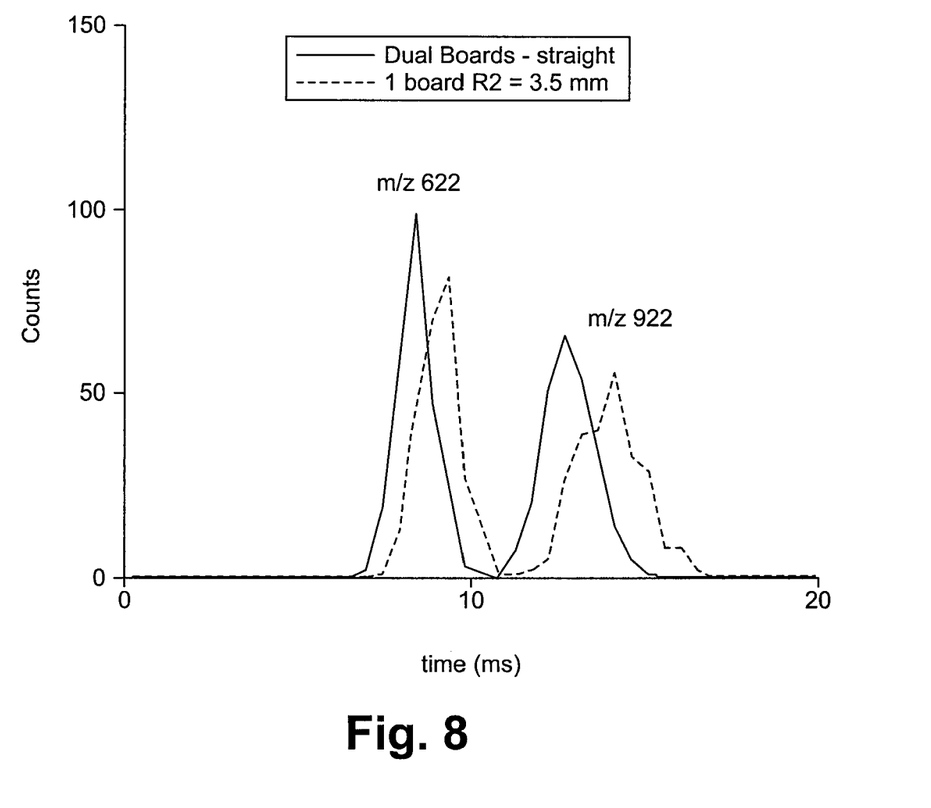
FIG. 8 is a plot of ion counts over arrival time of two ions with different mass-to-charge ratios, and separated according to their mobilities, using two different configurations—the embodiment of FIG. 4 or a single board ion mobility separation device and a prior dual board ion mobility separation device.

FIG. 8 is a plot of ion counts over arrival time of two ions with different mass-to-charge ratios (m/z 622 and m/z 922) using two different configurations—the embodiment of FIG. 4 or a single board ion mobility separation device and a prior dual board ion mobility separation device. The prior dual boards are straight or planar, while the single board configuration is curved. The length of each device is approximately 76 mm.

Figure 9A:
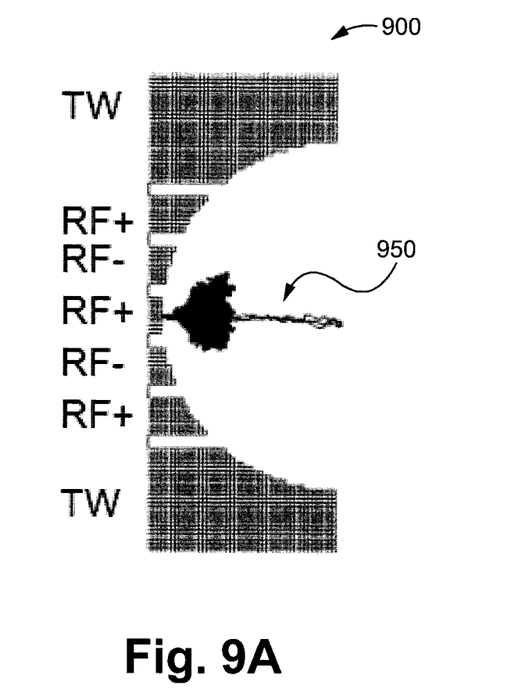
FIGS. 9A and 9B show a cross section and three-dimensional schematic diagram, respectively, of the ion mobility device of FIG. 2, with ions moving through the device at a distance from the surface, with a DC traveling wave field applied to the outside electrodes and opposing phases of RF applied to the inner electrodes, in accordance with one embodiment of the present invention.
Figure 9B:
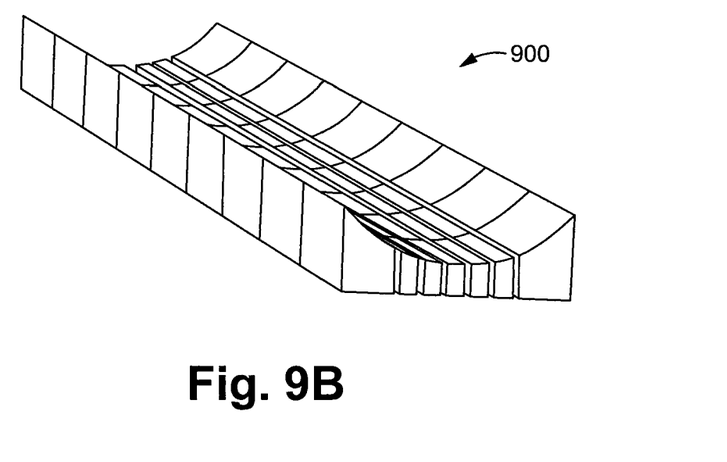

FIGS. 9A and 9B show a cross section and three-dimensional schematic diagram, respectively, of the ion mobility device of FIG. 2, with ions moving through the device at a distance from the surface, with a DC traveling wave field applied to the outside electrodes and opposing phases of RF applied to the inner electrodes, in accordance with one embodiment of the present invention.

Figure 10A:
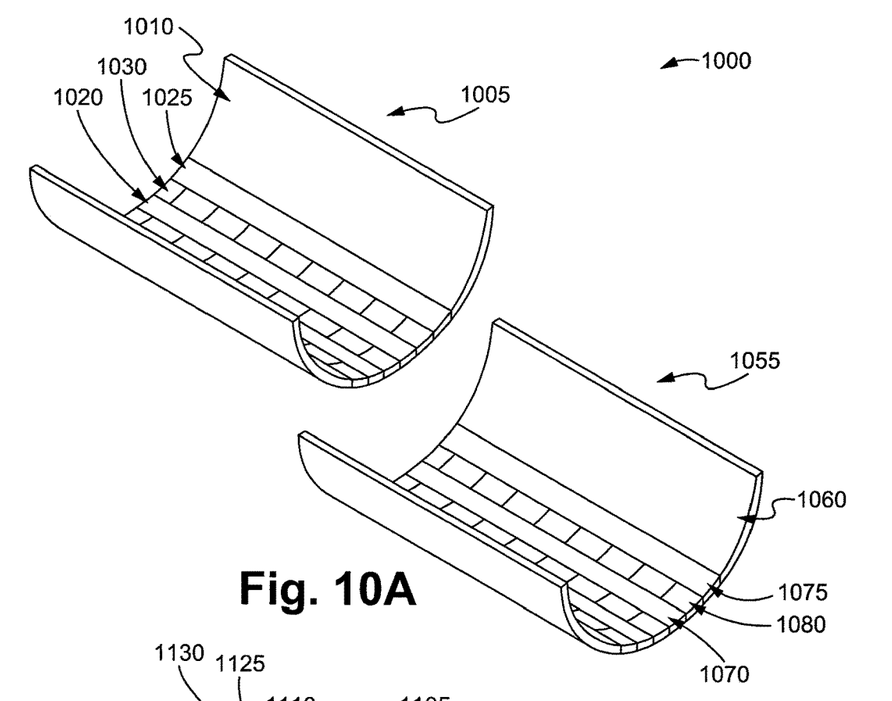
FIG. 10A is a perspective view schematic diagram of two devices, each similar to the embodiment shown in FIGS. 1A-D, with one device above and offset from the other at an angle, to provide a "waterfall" effect of the ions traveling from one device to the other.

FIG. 10A is a perspective view schematic diagram of two devices 1005 and 1055 used in combination as an ion mobility separation device or apparatus 1000. Each device 1005 and 1055 is similar to the embodiment shown in FIGS. 1A-D, with one device 1005 above and offset from the other 1055 at an angle, to provide a "waterfall" effect of the ions traveling from one device to the other.

The device 1005 includes outer arrays of DC electrodes 1010, inner arrays of DC electrodes 1030, and arrays of RF electrodes 1020 and 1025. Each inner array of DC electrodes 1030 is positioned between an array of RF electrodes 1020 and 1025 having opposite phases (RF+ or RF−).

The device 1055 includes outer arrays of DC electrodes 1060, inner arrays of DC electrodes 1080, and arrays of RF electrodes 1070 and 1075. Each inner array of DC electrodes 1080 is positioned between an array of RF electrodes 1070 and 1075 having opposite phases (RF+ or RF−).

Figure 10B:
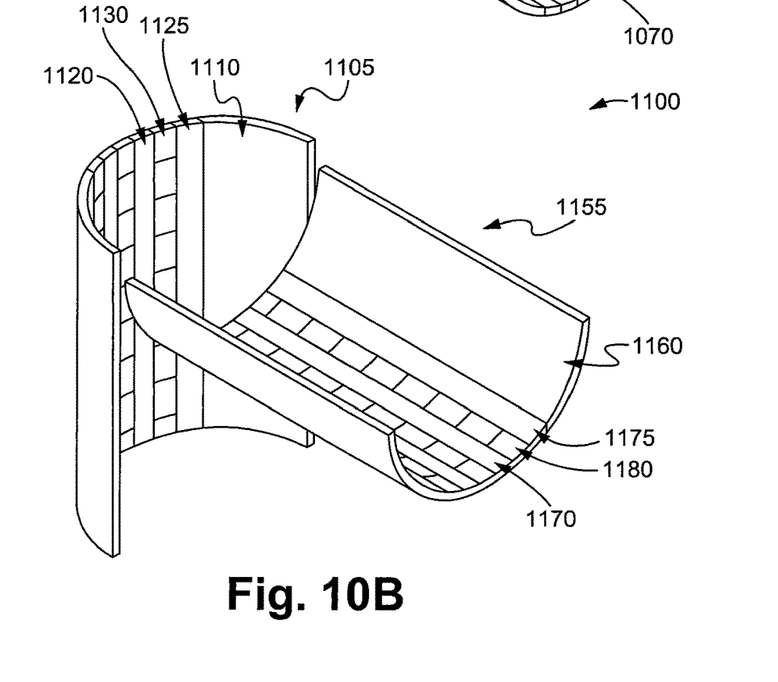
FIG. 10B is a perspective view schematic diagram of two devices, each similar to the embodiment shown in FIGS. 1A-D, with the devices positioned orthogonally to one another, to provide a "waterfall" effect of the ions traveling from one device to the other.

FIG. 10B is a perspective view schematic diagram of two devices 1105 and 1155 used in combination as an ion mobility separation device or apparatus 1100. Each device 1105 and 1155 is similar to the embodiment shown in FIGS. 1A-D, with the devices 1105 and 1155 positioned orthogonally to one another, to provide a "waterfall" effect of the ions traveling from one device to the other.

The device 1105 includes outer arrays of DC electrodes 1110, inner arrays of DC electrodes 1130, and arrays of RF electrodes 1120 and 1125. Each inner array of DC electrodes 1130 is positioned between an array of RF electrodes 1120 and 1125 having opposite phases (RF+ or RF−).

The device 1155 includes outer arrays of DC electrodes 1160, inner arrays of DC electrodes 1180, and arrays of RF electrodes 1170 and 1175. Each inner array of DC electrodes 1180 is positioned between an array of RF electrodes 1170 and 1175 having opposite phases (RF+ or RF−).

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. An ion mobility manipulation device comprising:
   a non-planar surface comprising a first, second and third region;
   an inner array of electrodes positioned on the first region, a first set of electrodes of the inner array of electrodes configured to receive RF voltages and generate a first potential upon the receipt of the RF voltage; and
   a first and second outer arrays of electrodes coupled to the second and third region, respectively, the first and second outer arrays configured to receive a first DC voltage and generate a second potential upon the receipt of the first DC voltages,
   wherein the first and second generated potential manipulate movement of ions.

2. The device of claim 1, wherein the non-planar surface is curved to form an ion channel, wherein movement of ions occurs in the ion channel.

3. The device of claim 2, wherein the inner array of electrodes, the first and second outer arrays of electrodes and the ionization separation channel extend along a length of the device.

4. The device of claim 2, wherein the first outer array of electrodes is positioned on a first side of the inner array of electrodes, and the second outer array of electrodes is positioned on a second side of the inner array of electrodes.

5. The device of claim 2, wherein the inner array of electrodes comprises a second set of electrodes configured to receive a second DC voltage.

6. The device of claim 5, wherein the second set of electrodes generate a gradient potential that drives the ions in the ion channel.

7. The device of claim 5, wherein electrodes of the first set of electrodes are separated by electrodes of the second set of electrodes.

8. The device of claim 2, wherein the first set of electrodes of the inner array of electrodes is configured to receive a second DC voltage.

9. The device of claim 8, wherein RF voltages received by neighboring electrodes of the first set of electrodes are phase shifted.

10. The device of claim 1, wherein the second potential confines the ions along a lateral direction associated with the device.

11. The device of claim 1, wherein RF voltages received by adjacent electrodes of the first set of electrodes have a phase difference.

12. The device of claim 11, wherein the phase difference is 180 degrees.

13. The device of claim 1, wherein the first generated potential inhibits the ions from approaching the non-planer surface.

14. The device of claim 1, further comprising a cover enclosure, wherein the cover enclosure is configured to guard against an external potential.

15. The device of claim 14, wherein the cover enclosure is configured to receive a potential.

16. The device of claim 1 wherein the non-planar surface is one of the following shapes: cylindrical, a spiral, a funnel, hemispherical, or elliptical.

* * * * *